United States Patent [19]

Neumeyer

[11] Patent Number: 5,181,850

[45] Date of Patent: Jan. 26, 1993

[54] MECHANICAL CONNECTING ELEMENTS

[76] Inventor: Stefan Neumeyer, Leminger Strasse 10, 8491 Eschlkam, Fed. Rep. of Germany

[21] Appl. No.: 807,970

[22] Filed: Dec. 12, 1991

Related U.S. Application Data

[63] Continuation of Ser. No. 276,758, Nov. 28, 1988, abandoned.

[30] Foreign Application Priority Data

Nov. 27, 1987 [DE] Fed. Rep. of Germany ....... 3740192
Mar. 30, 1988 [DE] Fed. Rep. of Germany ....... 3810857

[51] Int. Cl.$^5$ ......................... A61C 13/08; A61C 5/08
[52] U.S. Cl. ..................... 433/205; 433/220; 433/221
[58] Field of Search .................. 433/220, 221

[56] References Cited

U.S. PATENT DOCUMENTS

| | | | |
|---|---|---|---|
| 1,936,333 | 11/1933 | Maulen | 433/211 |
| 2,227,735 | 1/1941 | Morton | 433/219 |
| 3,590,486 | 7/1971 | Brenner | 433/225 |
| 3,740,851 | 6/1973 | Weissman | 433/225 |
| 4,600,391 | 7/1986 | Jacob | 433/221 |

FOREIGN PATENT DOCUMENTS

| | | | |
|---|---|---|---|
| 170872 | 7/1934 | Fed. Rep. of Germany | 433/210 |
| 2162068 | 1/1986 | Fed. Rep. of Germany | 433/221 |
| 3427172 | 1/1986 | Fed. Rep. of Germany | 433/225 |
| 3504472 | 7/1986 | Fed. Rep. of Germany | 433/225 |
| 3524556 | 1/1987 | Fed. Rep. of Germany | 433/211 |
| 3839466 | 1/1989 | Fed. Rep. of Germany | 433/225 |
| 3905126 | 9/1989 | Fed. Rep. of Germany | 433/220 |
| 1160841 | 4/1958 | France | 433/265 |
| 2230333 | 12/1974 | France | 433/225 |

Primary Examiner—Gene Mancene
Assistant Examiner—Cindy A. Cherichetti
Attorney, Agent, or Firm—Hoffman, Wasson & Gitler

[57] ABSTRACT

A supporting mechanical connecting element of metal or the like high-strength material, preferably for the medical and dental field, is formed so that the connecting element and/or the receiving element is coated with a hydrolysis-stable bond-assisting layer undergoing a hydrolysis-stable chemical or physical-chemical bond with the material of the receiving element. In order to improve the mechanical retention the connecting element being used for anchoring has a cylindrical shaft, a circular portion conically tapering towards the free end and a circular, in cross section U-shaped recess extending from the free end inwardly, whereby this form is chosen so that it results in a tension reduction.

28 Claims, 7 Drawing Sheets

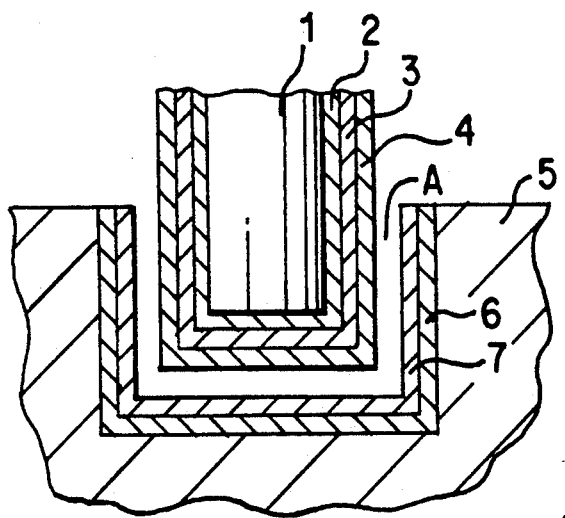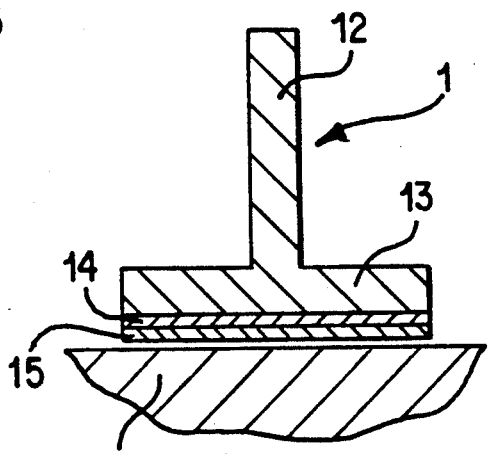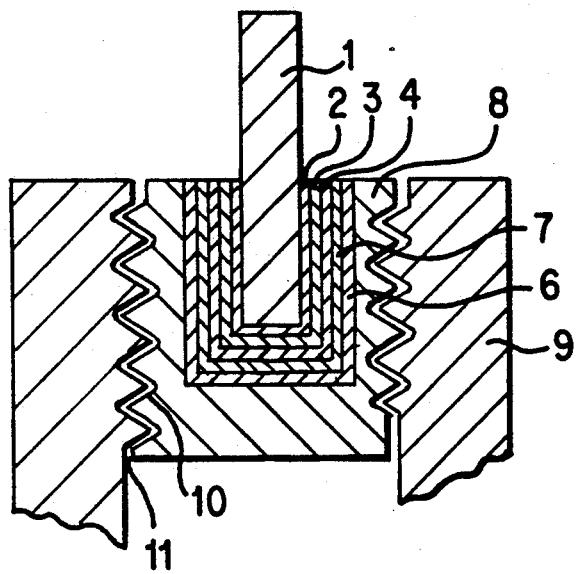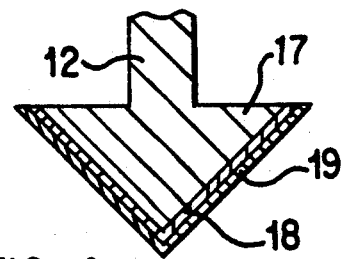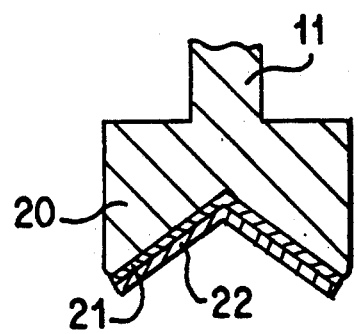
FIG. 1
FIG. 3
FIG. 2
FIG. 4
FIG. 5

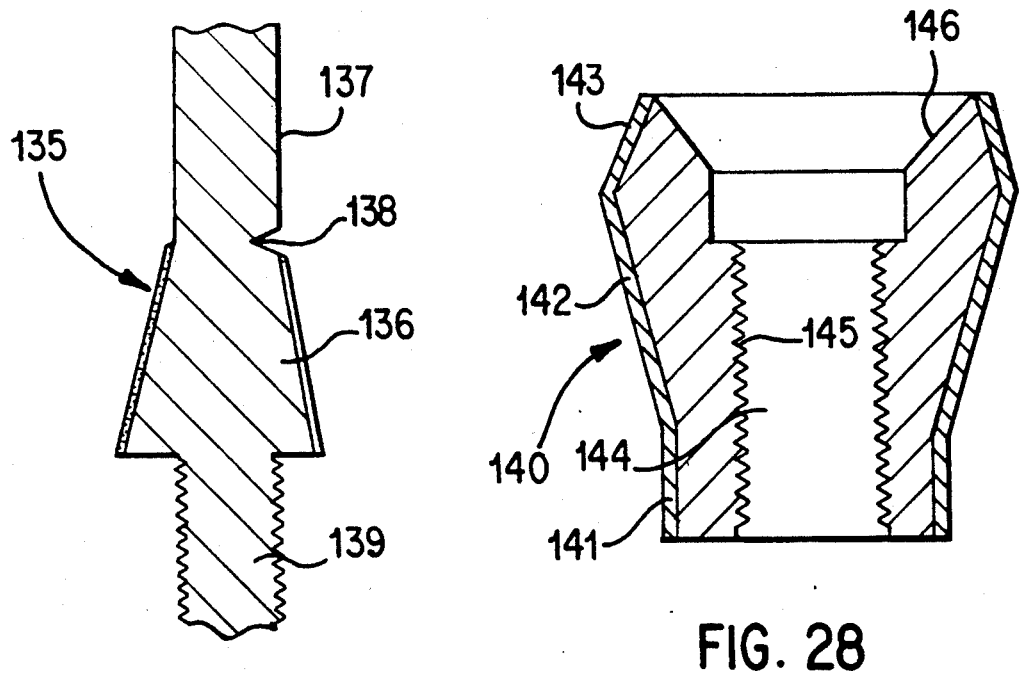
FIG. 27
FIG. 28
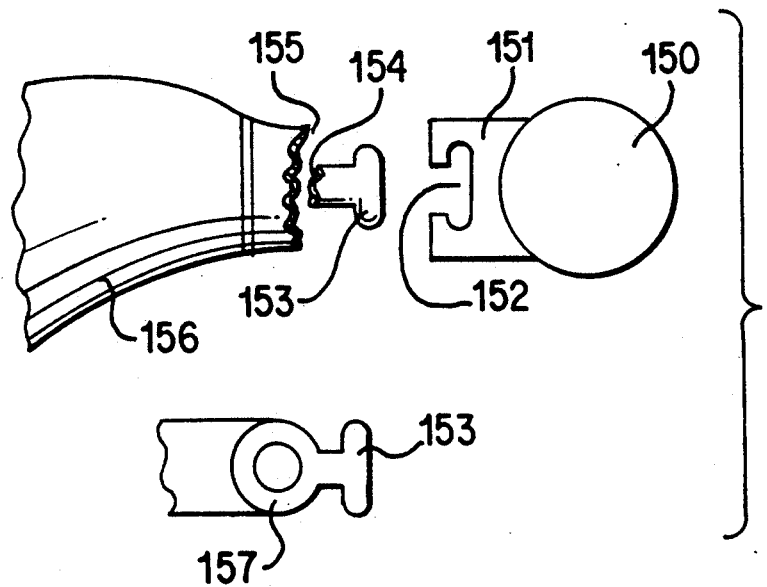
FIG. 31

MECHANICAL CONNECTING ELEMENTS

This is a continuation of copending application Ser. No. 07/276,758 filed on Nov. 28, 1988 now abandoned.

BACKGROUND OF THE INVENTION

This invention refers to supporting mechanical connecting elements made from metal or similar material of high strength, such as pins, bolts, sleeves or the like elements to be connected with a receiving element, which also can be a receiving wall or a receiving plate (made from glass, ceramics, metal, plastics or the like material), or for connecting two supporting elements with each other. The preferable field of this invention is medicine, dental medicine and dental technique.

There are known the most different forms and types of screws, bolts, pins, etc., one end of which is inserted into a wall or a structural element and is fastened therein, and the other end of which receives the element to be connected or to be fastened. Usually, screws are inserted or plastered into a wall by means of dowels—in order to obtain high supporting power special dowels are available. In certain cases screws and bolts also are bonded with supporting walls.

All known connections of this type have the disadvantage that sealing means are required around the bolts or screws, if water or moisture is able to get access to the connecting areas; this is also true for adhesive connections because even adhesive areas made with epoxy adhesives are dissolved by water in the long term; this results in corrosion effects with all the disadvantageous sequences. Furthermore, the connecting areas of such mechanical connections merely have a limited strength and supporting capacity. In addition, with many materials as glass or ceramics, cracks will result from too heavy tightening of the screws, and it is difficult to drill holes through such materials for inserting screws or dowels.

If this type of connecting elements is to be used for the medical and dental field a mechanical connection is obtained between the connecting element and the tooth substance the retention force of which is relatively low in view of the existing high forces, and in view of the microedge gap.

SUMMARY OF THE INVENTION

It is an object of this invention to provide mechanical connecting elements, such as metal pins, metal sleeves or the like, in such a manner that their retention force is considerably increased. It is a further object of this invention to provide the mechanical connecting elements with a coating resulting in a bond with the supporting, surrounding material, which has an optimum strength and which is free of tensions and is corrosion-resistive. Another object of this invention is to provide the mechanical connecting elements with a shape based on which a higher retention force will be obtained. A still further object of this invention is to use this type of connection elements for the medical or dental field in order to obtain a retention with the material supporting the connecting element in a most simple and secure manner, which retention is by far superior to any retention, which can be obtained with known connecting elements.

According to this invention these objects and problems are solved by coating the connecting element and/or the supporting element at least partly with a hydrolysis-stable bond-assisting-layer, f.e. $SiO_xC$—, metal ceramics or plastic layer, which is connected to the material of the supporting element in such a manner that it undergoes a hydrolysis-stable chemical or physical-chemical bonding. Furthermore, this invention proposes an anchoring connecting element having a cylindrical shaft, a circular-symmetrical tapering with decreasing diameter towards the free end, and a circular-symmetrical, in cross section U-shaped tapering, which extends from the free end inwardly, said shape being chosen so that it results in a reduction of the tension. The connecting element can be roughened over at least part of its surface, and the degree of roughness is optimized in view of the strength of the material to be anchored.

This type of hydrolysis-stable intermediate layer in the form of a bond-assisting layer upon the connecting element, for example a metal pin or a metal sleeve, allows to bond the metal surface of the connecting element with the supporting element with extreme strength and density so that the bond is loadable to a higher extent than the material of the connecting element itself, and—if there is a danger of corrosion to dispense with any type of additional sealing means, because both parts undergo a chemical bond. The area of the surface, on which said bond is obtained, is considerably larger than with a mechanical connection. This surface area still can be increased by providing the surface of the connecting element with threads, projections and depressions, rougheninings, and the like within the surface structure in a special manner. This allows to increase the anchoring force of the connecting element manifold compared with a mere mechanical connection.

The intermediate layer formed as a bond assisting layer is applied onto the connecting element already at the production site so that the commercially available pin, sleeve, or the like is obtained at the consumer, namely the dentist, already provided with an intermediate layer. The type of intermediate layer depends on the material with which the pin or the sleeve is to undergo a chemical bond; accordingly, different types of pins or sleeves can be used for different receiving materials.

The intermediate layer is applied onto the connecting element, namely a metal pin or a metal sleeve by being shrinked, bonded, sprayed, or in any other known manner as a layer either across the entire surface of the connecting element or alternatively across part of said surface leaving another part of the surface uncoated, which part can be made of magnetic material so that at these uncoated areas the connecting element is magnetizable. The coated, commercially available connecting element, esp. a pin, preferably is inserted into a correspondingly formed bore of a sleeve, a wall or the like, whereby the recess is provided with an adhesive or bonding material, which undergoes a firm connection with the bond-assisting layer of the pin or the like so that altogether a chemical compound is obtained. If this type of pin or the like is to be used as a connecting element for a plate or a similar element made of plastics, ceramics, glass or the like, this element does not require any additional screwing means. Rather, a borehole is drilled, the coated pin or the like element is inserted into said borehole, is bonded therein and after a predetermined time of hardening a connection of extremely high strength is obtained.

If the pin or a similar element is to be connected with a structural element made of ceramics, glass, or the like material the surface of the said structural element is roughened at the joint, a silane-bond-assisting material and upon thereof a liquid plastics material as a connecting layer is applied. With this structure the pin or the like is connected, which pin is coated with a silane-bond-assisting material and those points or areas to be connected with the ceramics element, and at its outer side is provided with a cover layer, which is a plastics layer.

The pin, bolt, or the like element with the bond-assisting layer can be provided with a further, outer layer covering the bond-assisting layer and preventing its damage. This layer is a protective layer, which also can be made so that it is used as a projection for applying a tool, such as a polyhdral head.

The retention forces of connecting elements having a physical-chemical or alternatively a purely chemical compound are—as detailed experiments have shown—by far higher than mechanical retention systems with a thread, whereby the retention force still can be improved by roughening the metal surface of the connecting elements. The coating of the connecting element which results in the chemical compound can be set up in different structures, as follows:

A silica-carbon-layer is applied, for example according to the known silicoater procedure onto the connecting element, which can be a pin. This layer together with the surface of the pin or the like, which preferably made from metal and the peripheral surface of which is roughened, f.e. by sand blasting, undergoes an intimate adhesive or physical bond. Onto this $SiO_x$-C-layer a silane bond-assisting layer is applied, which results in a chemical bond with the plastics material forming the outermost layer of the completed pin, which undergoes a chemical bond with the material of the supporting element.

According to another embodiment of the invention a tin-oxide or similar metal oxide layer is applied onto the roughened pin, and this layer is provided with a tin-oxide, titanium-oxide, or the like bond-assisting-layer, and upon this layer as the outermost layer a layer of plastics material is applied. The connections between the individual layers are chemical bonds. Alternatively, instead of tin-oxide tin sulfide, which is difficult to dissolve, or instead of titanium-oxide titanium-sulfide can be used, which results in very good reactions with the bond-assisting material.

With a further embodiment of the invention the pin or the like element is made of titanium or a corresponding material, which under the influence of air forms a titanium-oxide at the surface or allows this oxide to be generated by means of a special procedure. Onto said titanium-oxide a bond-assisting material and upon that a plastics material is applied. Instead of titanium also other metals or the alloys thereof can be used as a material for the pin or the like element, the surface of which oxidizes. Also metal alloys, such as Ti-Va-Al-alloys can be used. Examples for such bond-assisting materials are titanates or 4-meta-opaque-resin.

This type of pin connection also can be formed in such a manner that the coated pin is inserted into a bore, sleeve or the like, which also is made of metal and is provided with a corresponding inner coating so that between pin and sleeve a chemical bond is obtained. The sleeve can be provided with a thread at its outer periphery and can be screwed into a thread provided within the borehole of a plate, a wall or a similar structural element.

With a connecting element formed as a metal pin, metal bolt or the like, the layer can be applied onto the pin itself or onto the borehole of the supporting plate or the like, which receives the pin; alternatively, the pin can be provided at one end with a head-like extension or a punch, which is made in one piece with the pin or is fastened to the pin, whereby the free surface of the punch is provided with the coating. This free surface also can be made a plane surface or can be different from the plane shape, f.e. in the form of an arrow the tip of which points outwards or inwards, whereby the surfaces of the arrow are provided with the coating.

A special way of using the pins according to this invention is to use this type of metal pin with a coating made from a bond-assisting material and an outwardly joining plastics material for connecting two adjacent teeth the two sides of which facing each other being provided with a recess each (made by drilling or by some other operation mode); said recess receives one end of the pin together with a filler material, which fills the recess so that the two teeth are firmly connected by means of this type of pin. The connection between pin and tooth material through the filler material again is a chemical bond and thus is resistive to the mouth liquid, is inert and is of high strength. The filler material can be a self-hardening plastics material, which bonds with the metal pin on the one hand and with the tooth on the other hand. Instead of forming the pin as a cylinder the pin can be T-shaped at both ends so that altogether a cross-section of an I is formed, which results in an improved mechanical anchoring.

With a further variety of the invention the connecting element is formed so that it is made of two telescopically arranged, preferably cylindrical tube- or sleeve-like elements, the tubelike element of larger diameter being provided with a bond-assisting layer on its inner surface and the tubelike element of smaller diameter being provided with the bond-assisting layer on its outer surface; if the two tubelike elements are fitted into each other the two bond-assisting layers cooperate and undergo a chemical, hydrolysis-stable bond.

Instead of a pin-like connecting element a metal sleeve can be used for mechanically receiving a supporting element or the like. The sleeve preferably is provided with an inner thread, into which a supporting element with an outer thread can be screwed. The outer surface of the sleeve is provided with a coating, which cooperates with a corresponding coating applied onto the surface of a borehole or a recess of a receiving plate or receiving wall and undergoes a chemical bond.

Furthermore, a pin or a bolt with an outer thread is proposed to be inserted into a bore of a tooth to be restored or an implant, which tooth or implant can be screwed into a sleeve provided with an inner thread, upon which a tooth structure is formed. The lower section of the pin is screwed or bonded into the bore of the tooth or the implant. The inner surface of the sleeve, which is provided with a thread over the entire length or part thereof, is screwed into the upper section of the pin or bolt. The upper end of the sleeve can be open or closed; in the latter case the sleeve is formed as a cap. The outer surface of the sleeve at least partly is provided with a bond-assisting layer, which undergoes a hydrolysis-stable chemical or physical-chemical bond with the material of the structure. This type of coating can have an opaquer layer and/or a layer of plastics material dependent on the material of the structure. The outer layer of the coating preferably is provided with a special roughening, a thread or the like in order to improve the mechanical connection between the sleeve and the structure and to obtain an as large adhering surface as possible. The roughening, the thread or the like can be provided over the entire surface or part thereof.

At its upper end the pin or bolt can have a radially extending projection, which engages the upper side of the sleeve; this projection can be disc-like, however, alternatively also can have one or several noses, fingers or the like and acts as a stop for the sleeve.

With another embodiment of this invention the pin or bolt is provided with a head formed as a stop and on its cylindrical shaft has a thread, which cooperates with another thread within a borehole of an implant being connected with a bone. The metal pin with head is completely or partly coated with a bond-assisting material, onto which an opaquer layer and possibly a plastics layer is applied. The outer surface of the coating is roughened in a special manner or is provided with a thread. The radial surface at the transition between the cylindrical section and the head section of the pin or bolt is in contact with the facing surface of the implant. Over the metal pin with head a tooth structure is formed the material of which undergoes a hydrolysis-stable chemical or physical-chemical bond with the bond-assisting material of the metal pin.

Bond-assisting layer, opaquer layer and plastics layer do not need to be continuous and be applied uniformly; they can be of varying thickness in order to control predetermined characteristics, namely mechanical, physical and chemical characteristics.

A connection according to this invention allows to fasten pins, bolts or the like with the plate made of ceramics, glass or the like material in such a manner that between both a positive chemical bond is obtained so that the area of connection is not influenced adversely either by air, moisture or similar conditions.

If increasing the retention force is obtained by means of a special shape of the pin a free end of the pin is provided with a recess, which is axially symmetrical and is U- or V-shaped in cross section or is made in the shape of a crater, whereas the outer surface of the walls restricting the crater taper conically in the direction of the opening of the crater so that the shape of the pin changes from a cylindrical shape into a frusto-conical shape with a central crater-like recess. With an alternative of this embodiment the conically extending free section is connected to the cylindrical part of the pin by a section, which extends conically outwardly, whereas the central recess is maintained substantially unchanged. These special shapes allow a more uniform transmitting of the forces at the pi so that the filling material surrounding these pins under load will not be forged. In addition, dependent on the pin material the surface is roughened, and an optimum structure is obtained for example for amalgam by using rough diamond grain. The surfaces can be coated in the prescribed manner, however, also can be coated with hydroxylapatite or tricalcium phosphate. Special effects can be obtained by applying the coating in a discontinuous manner across the surface in order be able to control the load distribution.

With this type of shape of the pin the head portion provided with the recess or the crater can be formed as a grid, f.e. a titanium grid, which is connected with the cylindrical pin. Onto this grid titanium plasma is sprayed, f.e. according to the plasmaphen-method so that the grid on its surface is partly covered by the titanium plasma particles and partly has open spots through which the bone tissue can grow if it will be used as an implant. The grid is preferably made so that the distance between the titanium plasma particles is about 200–300 $\mu$. The shape of this type of grid is circular with a central recess and extends from the cylindrical shaft of the pin outwardly and downwardly in a slightly conical manner and adjacent to the recess extends conically downwards and inwards. The cylindrical shaft of the pin has an inner bore with a thread, into which a screw bolt can be screwed.

This type of pin shape has the advantage that at predetermined preferred locations a higher load of the connection can be obtained. Special heavy-load locations are taken into account by extending the walls forming the recess or the crater, which means that the crater is made deeper. This type of shape is of special advantage for dental retention pins, because with this type of use an increased retention force is most important, if the retention pins are inserted into the tooth substance for conserving teeth, whereas nowadays an overdimensioned borehole for taking up an overdimensioned cylindrical pin is necessary. The coating layer, which undergoes a chemical bond with the metal of the pin has not only the object of a connection with high adhesion with the material surrounding the pin, namely filling material or the like, but is also used for controlling the load parameter, especially the strength which can be obtained.

The quality or strength of the connection in addition can be increased by roughening the outer surface of the layer applied to the pin so that the surface will be increased. The degree of roughness will be chosen according to the material, which is in contact with this layer. Roughness and strength of the surrounding material have a predetermined relation to each other. Materials with higher strength require a higher roughness coefficient for an optimum retention, materials of less strength require a lower roughness coefficient. The roughness can be obtained at the outer side of the coated metal pin by mechanical roughening, by embedding diamond particles into the coating layer, etc.. However, it is also possible to apply an attenuating layer onto the coating, which on its outer side is roughened or includes corresponding particles on the surface. With the special type of retention pin made from metal or an implant from metal in the shape of a pin a bond-assisting layer is applied onto the surface of the pin, at the top thereof a plastics layer is provided and above this plastics layer a further layer of a bond-assisting material is applied; these layers form an attenuation system, on the outer surface of which a further layer, f.e. a titanium layer is applied the surface of which is roughened or is provided with coarse particles.

The connecting element in the shape of a cylindrical pin can be provided with a screw thread at one end thereof. If the pin is provided with a crater-like recess, the outer periphery of the end opposite to the crater is provided with a screw thread, or an analog crater is formed with or without a screw thread; this type of structure is used for receiving a connecting element in order to reduce the existing tensions and for obtaining higher load.

A few preferred embodiments and ways of use of the connecting element according to this invention for the dental field are as follows:

1. Fastening a metal plate to a tooth to be treated: The metal plate is provided with a throughgoing bore with a thread, the tooth is provided with a coaxial, throughgoing bore. A connecting pin with thread in the area of the metal plate is inserted into the throughgoing bore; the pin has a bond-assisting layer, which undergoes a hydrolysis-stable chemical bond with the inner wall of the bore within the tooth so that the metal plate is fastened to the tooth in a firm and long-lasting manner.

2. Fastening a crown to a tooth or an implant to a bone: The tooth or alternatively a hip joint bone is provided with a bore for receiving the pin. Part of the pin extends beyond the tooth or bone and is received by a bore within the crown or the implant. The hydrolysis-stable connection between crown or implant and said pin is obtained by means of the bond-assisting layer applied onto the pin. The pin also can have a corresponding bond-assisting layer on its section fastened to the tooth or bone.

3. Applying a connecting pin to a ceramics or porcelain tooth for being fastened to a support structure (tooth substitute): According to known procedures within the anchoring tooth a recess had to be provided and a sleeve had to be inserted into this recess with which sleeve an anchoring pin had to be welded. According to this invention the connecting element coated with a bond-assisting layer is inserted directly into the bore and a hydrolysis-stable connection is obtained between pin and bore respective recess.

4. Metal pin with concentric bore and inner thread for receiving a screw element, with $SiO_x$ x C-silane-bond-assisting layer, which is inserted into a corresponding sleeve made of ceramics, as from alumina or the like biocompatible ceramics material or tricalcium phosphate and is connected therewith, and the inner surface of which is provided with a bond-assisting layer.

BRIEF DESCRIPTION OF THE DRAWINGS

FIG. 1 shows an embodiment of a connecting element with a supporting element according to this invention, FIG. 2 shows an alternative of a connecting element according to FIG. 1, FIG. 3 shows a special embodiment of a connecting element as a punch, FIG. 4 shows a revised embodiment of the punch according to FIG. 3, FIG. 5 shows a further embodiment of the punch according to FIG. 3, FIG. 21 shows in a schematic view a pin and a sleeve separated from each other, FIG. 22 shows pin or bolt and sleeve inserted into a borehole of a tooth, with indicated structure, FIG. 23 shows a further embodiment of a pin or bolt connection with an implant, FIG. 24 shows a special embodiment of the foot of the pin or bolt, FIGS. 25, 26, 27 show further embodiments of a pin or a bolt according to the invention, FIG. 28 shows another embodiment of a sleeve, FIG. 31 shows an embodiment for using the invention for an attachment device.

DESCRIPTION OF THE PREFERRED EMBODIMENTS

Figure 6:
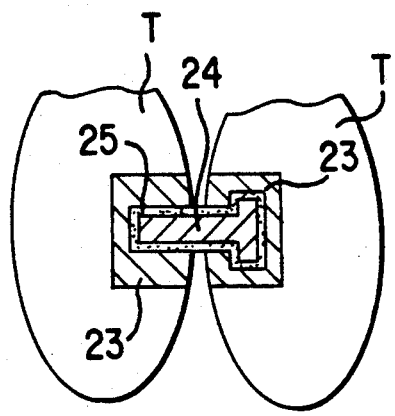
FIG. 6 shows the use of the pin connection for fastening two adjacent teeth with each other.

A connecting element, for example a pin or bolt 1 according to FIG. 1 is provided with a bond-assisting coating 2, such as $SiO_x$-C, a silane coating 3 and an outer plastics coating 4. The coatings or layers preferably are applied continuously and completely over the entire pin 1, however, also can be applied at will at certain areas, for example the head end, which is inserted into a recess A of the receiving element adapted to the shape of the head of the pin. The receiving element 5 can be a plate made of glass, ceramics or plastics and has a silane coating 6 within the recess A and a coating 7 made of plastics material, which undergoes a chemical bond with the plastics material of coating 4 of the pin. In FIG. 1 the plastics layers 4 and 7 are shown separate from each other, however, in practice dimensioning and fitting is chosen in such a manner that the plastics layers 4 and 7 are in contact and react with each other if the pin is inserted into recess A.

In addition to the chemical or alternatively physical-chemical bond between connecting element and receiving element an improved mechanical retention will be obtained by increasing the outer surface of the shank of the connecting element, for example by mechanically or chemically roughening the surface, by extensions and recesses provided at the outer periphery, by threads or the like.

According to the embodiment of FIG. 2 the pin 1 is formed similar to the pin of FIG. 1. The plastics layer 4 is in engagement with the plastics layer 7 of an intermediate body 8, which according to the picture of FIG. 1 is a silane layer 6. The intermediate body 8 is connected to a receiving element, f.e. a receiving plate or wall 9; a thread 10 can be provided on the cylindrical outer periphery of the intermediate body 8, whereas the supporting plate 9 is provided with a counter thread 11 so that the intermediate body 8 with pin 1 can be screwed into the supporting plate 9.

FIG. 3 shows a pin 1, which is formed of a shaft 12 and a punch body, which can be made in one piece with the lower end of the shaft 12; on the free end of the punch body 13 opposite to the shaft 12 a bond-assisting layer 14 and a plastics layer 15 are applied, which undergo a chemical bond with the supporting element 16 (which can be a plate). If the material of the supporting element 16 does not directly undergo a chemical bond with the plastics layer 15, a corresponding connecting system of a bond-assisting material and plastics material corresponding to system 14, 15 also is applied onto the supporting element 16 associated to the layers 14 and 15.

The operating surface of punch 13 is shown in FIG. 3 as a plane surface. In FIG. 4 the operation surface of punch 17 is formed conically, whereby the conical surfaces have a bond-assisting layer 18 and a plastics layer 19, which with a corresponding counter surface of the supporting element undergo a chemical bond. With a variation according to FIG. 5 the punch body 20 is formed conically the other way around; upon the conical surface of body 20 bond-assisting layer 21 and plastics layer 22 are applied.

The embodiment of the invention according to FIG. 6 refers to the use of the pin connection to the dental field. Two adjacent teeth T, T are provided with a recess 23 such as a borehole, which recesses face each other. A connecting pin 24 is inserted into each recess and is provided with a composite layer 25 as described. The recesses 23, 23 can be filled with filling material, which undergoes a chemical bond with the plastics layer of pin 24, and thus results in a simple and high-strength coupling of the two teeth with each other. The shape of the pin is of double-T or I-shape in cross section.

Figure 7:
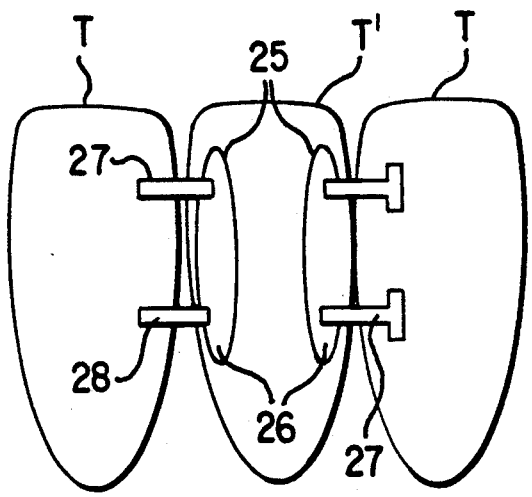
FIG. 7 shows the use of the pin connection for fastening a new tooth between two grown teeth.

With a different embodiment according to FIG. 7 a new tooth T' is inserted between two teeth T, T. Into both teeth T, T a carrier or a bridge 26, 27, 28 each is inserted, which consists of the two webs or pins 27, 28 and the connecting element 26, which is inserted into the new tooth T'. The connecting element 26 can be made from two parts by forming each of the webs or pins 27, 28 at the free end in T-shape. The connecting element 26 is coated as explained for FIG. 7.

Figure 8:
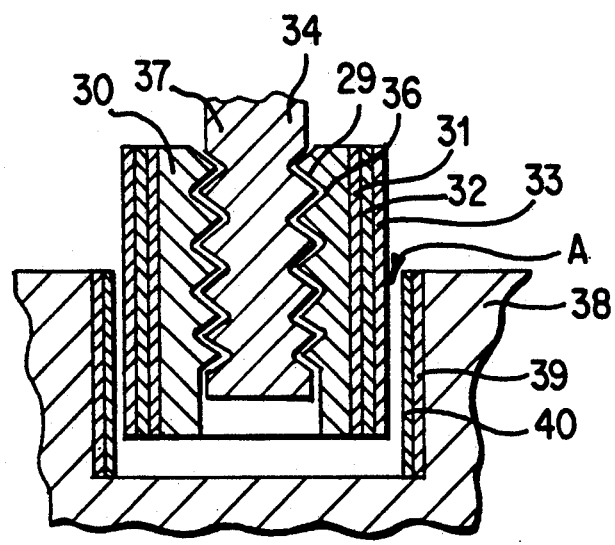
FIG. 8 shows another embodiment of the invention formed as a sleeve.

With the embodiment according to FIG. 8 instead of a pin element a metal sleeve 29 or a corresponding structural element is used. On its cylindrical outer surface this sleeve 29 is provided with a thread 30, with a roughened surface or an equivalent mechanical surface increase in order to obtain an improved bond with the outwardly joining layers. 31 is the bond-assisting layer, 32 the silane layer, and 33 the outer plastics layer. On its inner cylindrical surface the sleeve 29 can have a thread 36, which engages a thread 37 of a screw bolt 34. 38 is the supporting element, which has a recess A, a borehole or the like, on the cylindrical inner surface of which (and possibly at the bottom surface of which) a bond-assisting layer 39 and a plastics layer 40 are applied, which undergo a chemical bond with the plastics layer 33 of sleeve 29.

Figure 9:
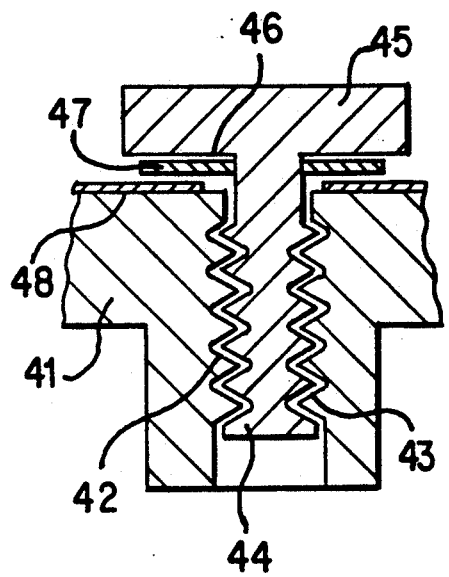
FIG. 9 shows a further embodiment of the invention formed as a screw connection.

Another embodiment of the invention is shown in FIG. 9. The supporting element, which can be a supporting plate 41, has a bore 42 with inner screw thread 43, into which a screw bolt 44 is screwed, which is provided with a screw head 45 in contact with the surface of the supporting plate 41. On the underside 46 of the screw head 45 a concentrical safety ring 47 is fastened, which results in a sealed connection with the upper side of plate 41 so that the access of moisture or the like into the screw shaft is prevented. A corresponding counter safety ring 48 can be arranged on the facing side of plate 41 in such a manner that the two safety or sealing rings 47 and 48 form a seal with each other. The sealing rings 47 and 48 are formed in a similar manner as the bond-assisting layers and plastics layers according to the preceeding embodiments so that a firm chemical bond is obtained between the safety ring 47 and the plate 41 or alternatively between the two safety rings 47 and 48.

Figure 10:
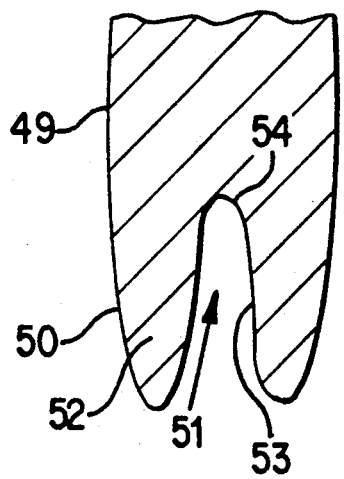
FIG. 10 shows a special embodiment of the structure of a pin connection according to the invention.
Figure 11:
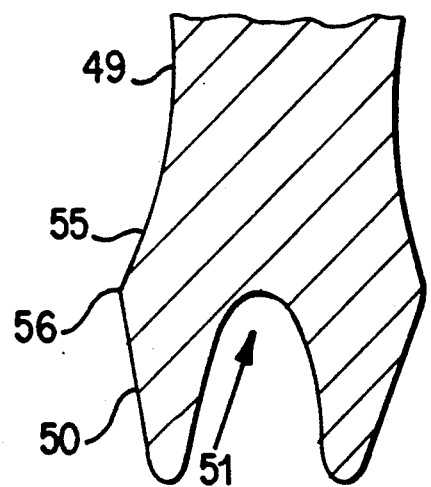
FIG. 11 shows an embodiment similar to FIG. 10.
Figure 12:
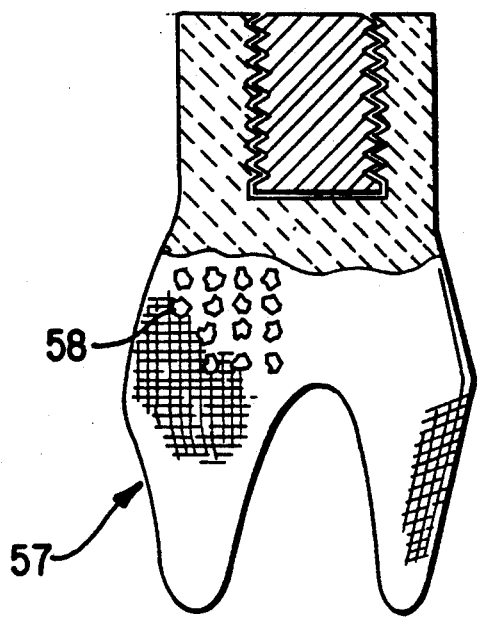
FIG. 12 shows a further embodiment of the structure of a pin connection.

The embodiments according to FIGS. 10, 11 and 12 refer to various shapes of connecting elements, especially connecting pins according to this invention, which allow an improved transfer of forces compared with known pins; this special shape of the pins is of major importance for the dental field, if such pins are used for restoring teeth. These pins are substantially cylindrical in shape; at one end the pin (outer wall surface 50) extends slightly conically downwards and inwards and at the lowermost position joins a recess 51, restriction or the like, which is axially symmetrical and is substantially U-shaped in cross section. This results in a crater shape the ringlike lateral wall 52 of which tapers conically outwards (indicated by 50 and 53), whereas the bottom of the crater is rounded at 54. The cylindrical shaft 49 of said pin according to FIG. 11 is followed by a downwardly and outwardly extending conical extension 55, which at the location 56 joins the downwardly and inwardly extending conical outer surface 50.

A cylindrical pin 49 according to FIGS. 10 and 11 can be provided with the same coatings as explained for the preceeding figures, however, the surface also can be coated with hydroxylapatite or tricalcium phosphate; furthermore, the coating can be of varying thickness at different locations and is not necessarily continuous. Preferably, the surface of the pin, especially at the areas 50, 53, 54 and 55, is roughened or treated in such a manner that an increase of the surface is obtained; a layer with diamond grain will result in an optimum roughening for the material surrounding the pin, which material can be amalgam.

With a revised embodiment according to FIG. 12 the lower part or head of the cylindrical pin can be produced separately from the cylindrical pin and can be made in the form of a grid basket 57 of the same shape as the end of the pin according to FIG. 10 or 11. The grid basket 57 consists of very fine grid with a mesh of 200-300 $\mu$. The grid preferably is a titanium grid, on which titanium plasma 48, (according to the plasmaphen procedure) is sprayed on. The mesh aperture is sufficient in order to allow the growing of a bone tissue through the grid so that this type of grid can be inserted as a genuine implant.

Figures 13, 14:
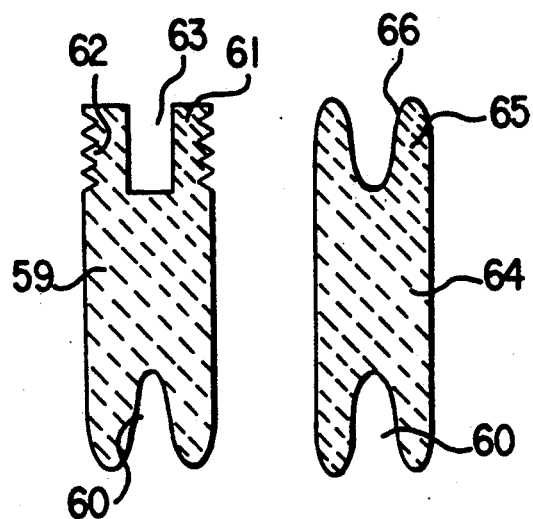
FIGS. 13 and 14 show further structures of a pin connection.

The embodiments according to FIGS. 13 and 14 show connecting elements according to those of FIG. 10, whereby the pin 59 according to FIG. 13 is provided with a thread 62 on its outer periphery at its end 61 opposite to the crater 60; by means of this thread the pin can be screwed into a receiving structure. In addition thereto, at this end a recess 63 can be provided, into which an extension of the receiving structure can be inserted. With the connecting element 64 according to FIG. 14 the end 65 opposite to the crater 60 is provided with a crater-like recess 66 so that the pin 64 has a substantially symmetrical shape.

Figure 15:
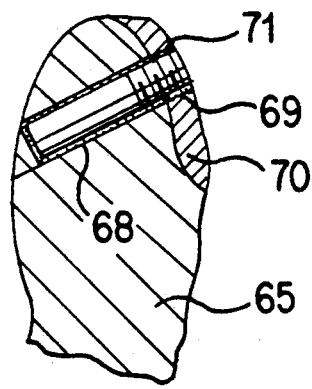
FIG. 15 shows a special embodiment and structure of a connecting element according to the invention.

According to the embodiment of FIG. 15 the tooth 65 is provided with a transverse wall 66, into which a connecting element, namely pin 67 is inserted, which has a bond-assisting layer 68 and a thread 69 at one end thereof. A metal plate 70 or a metal construction is fastened to the tooth 65. The shape of the plate follows the associated surface of the tooth, and the plate is provided with a bore 71 with inner thread in alignment with the bore 66 within the tooth so that the threaded portion 69 of pin 67 can be screwed in. Accordingly, pin 67 is inserted into the tooth 65 in a hydrolysis-stable manner with a chemical bond, and in addition is fastened with the metal plate mechanically. Metal plate 70 can be a metal structure for fastening the tooth 65 or the like.

Figure 16:
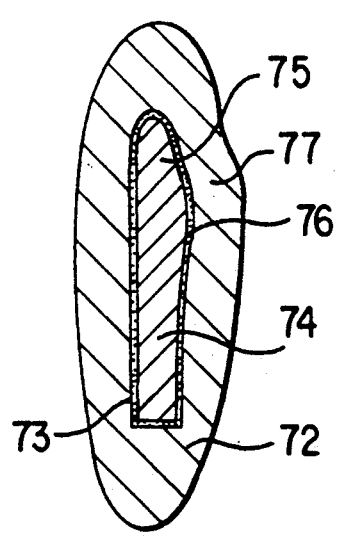
FIG. 16 shows a further embodiment and use of the invention.

The embodiment according to FIG. 16 shows a broken and cut tooth 72 or a bone having a bore 73 for receiving a pin 74 or a similar connecting element. Pin 74 can be screwed into the bore 73 of the tooth or bone 72 and/or can be inserted therein by means of a chemical bond. Section 75 of pin 74 extends beyond the tooth and is provided with a bond-assisting layer 76, which produces the chemical bond to the receiving element formed as a crown 77. Instead of a crown 77 for setting up a tooth an implant in connection with certain bones of the human bone system can be used.

Figure 17:
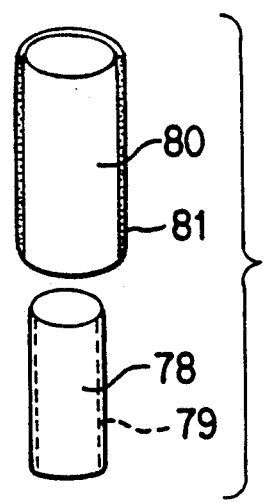
FIG. 17 shows another embodiment of a connecting element according to this invention.

FIG. 17 shows another embodiment of a connecting element according to this invention made as a tube 78 having a bond-assisting layer 79 on its outer peripheral surface. Tube 78 is associated to a tube 80 of larger diameter, which is provided with a bond-assisting layer 81 at its inner surface. The two tubes 78 80 are dimensioned so that they fit into one another, and are chemically bonded with each other by means of the bond-assisting layers 79, 81, similar to the bond between a pin-like connecting element and an associated supporting element.

Figure 18:
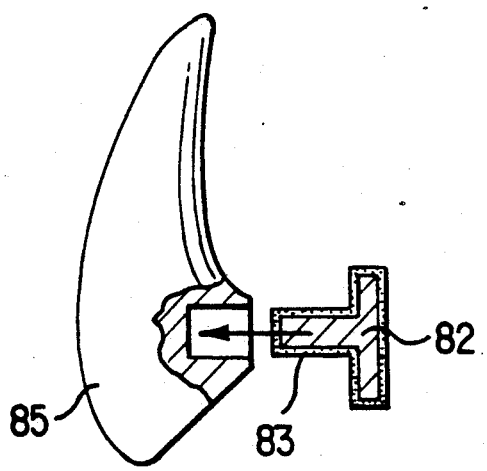
FIG. 18 shows a further example of the way of using a connecting element according to this invention.

For fastening a tooth made of ceramics material having a connecting element, especially a pin, with a supporting element, the pin according to the state of the art is fastened by means of soldering material within a sleeve, which is inserted into a bore of the ceramic tooth. In order to simplify such complicated and expensive procedure, according to FIG. 18 a pin 82 with a bond-assisting layer 83 is inserted into the bore 84 of the ceramics tooth 85 and is chemically bonded with the ceramics material so that a hydrolysis-stable and undetachable anchoring of the pin within the ceramic tooth is obtained.

Figure 19:
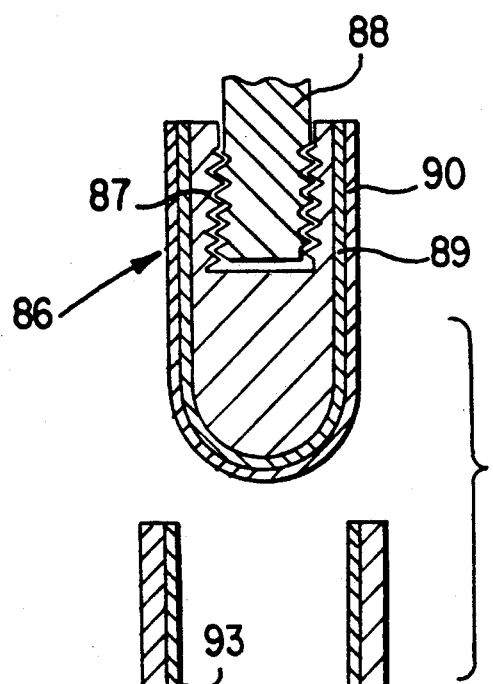
FIG. 19 shows a still other embodiment and way of use of a connecting element according to this invention.
Figure 20:
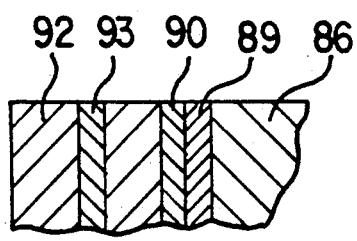
FIG. 20 shows an embodiment for the structure of layers of the embodiment according to FIG. 19 or preceeding Figures.

Another embodiment of a connecting element in the form of a pin associated to a supporting element, namely a receiving sleeve, is shown in FIG. 19. The metal pin 86, which at one end has a recess 87 with a thread for receiving a screw bolt 88 is provided with a $SiO_x$-C—layer 89, and an outside bond-assisting layer 90. This pin is inserted into a ceramics sleeve 91, the inner wall 92 of which is adapted to the shape of the pin 86 and has a bond-assisting layer 93, which undergoes a chemical bond with the bond-assisting layer 90 of the pin so that sleeve and pin can be bonded in a firm and hydrolysis-stable manner. The sequence of layers of the combination of pin and sleeve is schematically shown in FIG. 20.

Figures 21, 22, 25:
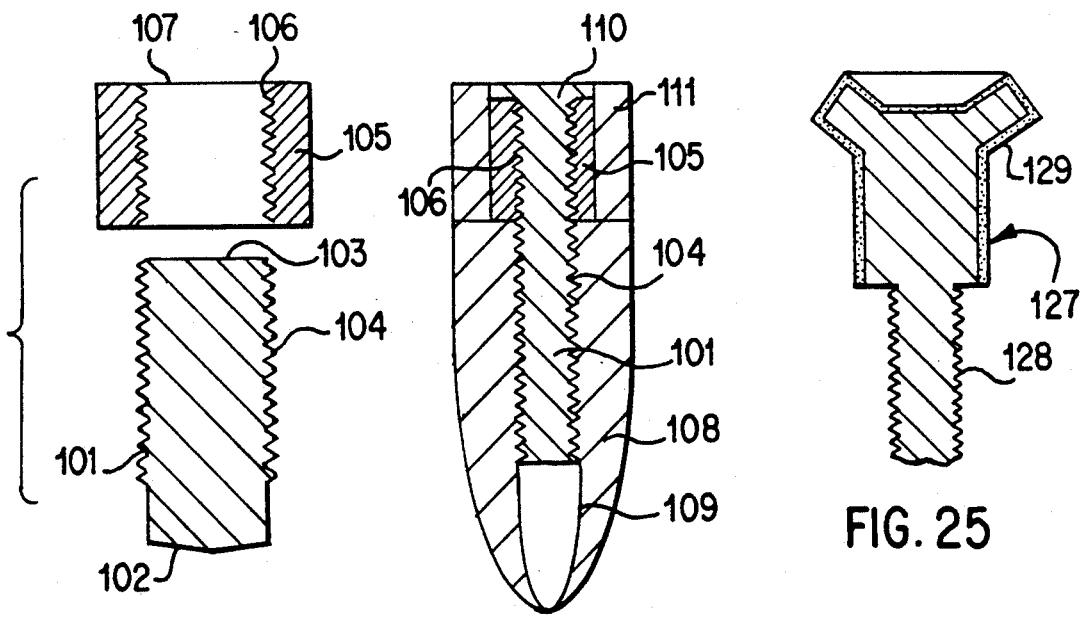

FIG. 21 shows a pin or bolt 101 the lower end 102 of which either is flat or slightly inclined towards the centre, whereas the upper side 103 is also plane or, as shown in FIG. 22, is widened with an increased radius. The peripheral surface of the pin or bolt 101 is provided with a thread 104. Sleeve 105 has a counter-thread 106, which engages thread 104 on its inner side. This sleeve according to FIG. 21 is open at the top 107, however, it can also be formed as a cap, which means that it is closed on one end.

In FIG. 22 the pin or sleeve 101, 105 is shown in connection with a tooth 108 to be restored; the tooth has a bore 109 into which the lower portion of the pin with thread 104 is screwed. The upper end of pin 101 is provided with a circular extension 110, which also can extend outwardly in steps, and which is used as a stop for sleeve 105, if the pin is connected to the sleeve. The tooth structure is marked 111, which is formed around the sleeve 105 and the upper portion of pin 110 for restoring the tooth.

Figures 23, 24, 26:
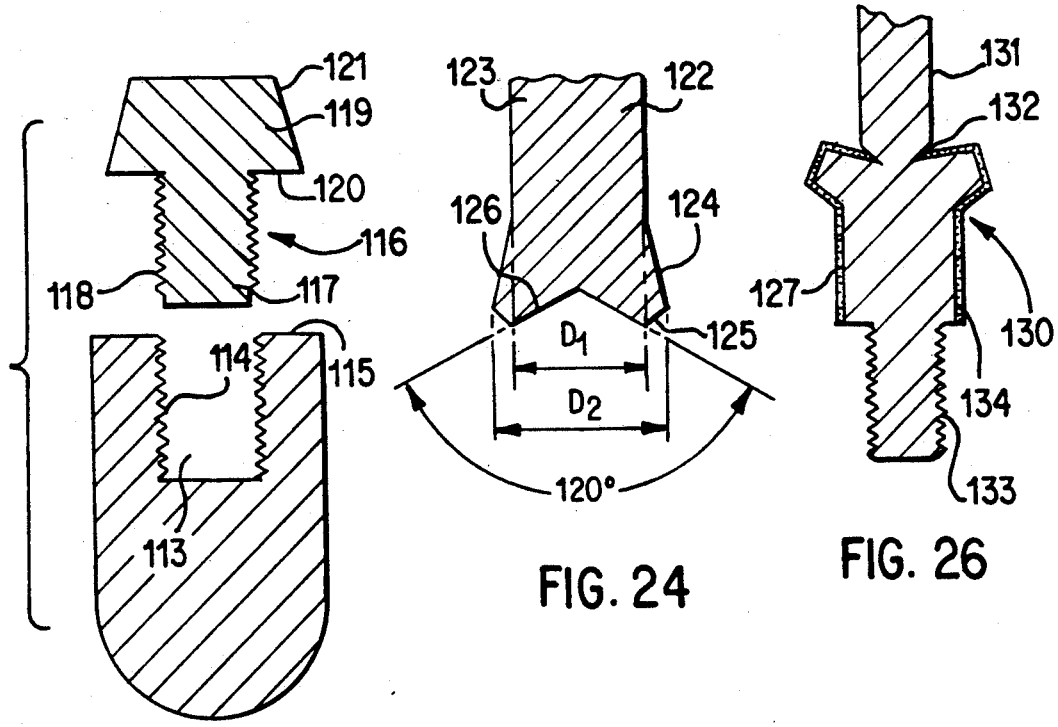

FIG. 23 shows an implant 112, which is inserted into a bone or is part of a bone. On its upper side said implant has a bore 113 with an inner thread 114. The upper end of the implant is marked 115. The pin or bolt 116 has a shaft 117 with a thread 118, which is in engagement with the inner thread 114 of the implant, as well as a head 119, the lower end 120 of which acts as a stop for the upper side 115 of the implant. Shaft 117 can be provided with a coating 121, which covers the peripheral surface of the pin or bolt 116 completely or partly. This coat consists of a bond-assisting layer, upon which an opaquer layer and upon the latter a plastics layer can be applied. In addition to the thread, the outer side of the coating can be roughened in a special manner in order to increase the surface. If a bond-assisting layer is used a thread at the bolt shaft possibly can be dispensed with.

With a special embodiment of the invention the implant within the lower (epital) area is porous, perforated, spongy or the like, and can be made of titanium. The pores either are continuously of equal size or increase or decrease in diameter. The porous lower portion of the implant is connected with the body part, for example by bonding or burning up. The pin or bolt 122 according to FIG. 24 at its foot end has a downwardly and outwardly extending, slightly conical section 124, which starts from the cylindrical shaft 123, followed by a conical section 125, which extends downwardly and inwardly, and a tapered section 126, which joins section 125 and extends inwardly and upwardly. The length of the conical section 124 is 0,65, the length of the conical section 125 is 0,15, and the depth of the taper 126 is 0,25 (related to the entire length=1,0); the tapering aperture has an angle of 120°, diameter $D_1$ according to a special embodiment is 0,9 mm, diameter $D_2=1,14$ mm, and diameter $D_3$ is also 0,9 mm.

FIGS. 25, 26 and 27 show further embodiments of a pin or bolt. Pin 127 of FIG. 25 has a head portion 127, which corresponds to that of FIG. 24; the head portion 127 has a shaft 128 with a thread, which can be inserted into an implant 112 similar to the embodiment of FIG. 23. 129 shows a coating similar to coating 121 of FIG. 23. Pin or bolt 130 according to FIG. 26 corresponds to that of FIG. 25, however, this pin is provided with an extension 131 for screwing the pin as well as with a breaking point 132, at which the extension 131 is released from head 127 when being screwed in. Pin 130 also has a shaft 133 with a thread, whereas the head is provided with a coating 134. Pin 135 according to FIG. 27 is similar, the head 136 tapers towards the extension 137 and a breaking point 138 is provided at the transient area. Shaft 139 again has a thread.

FIG. 28 shows a sleeve 140, which has a cylindrical section 141, an outwardly tapering section 1142 and starting therefrom an inwardly tapering section 143 (similar to the shape of the pin according to FIG. 24);

however, the sleeve has an inner bore 144 with thread 145 and is conically widening outwardly beyond the thread at 146.

Figure 29:
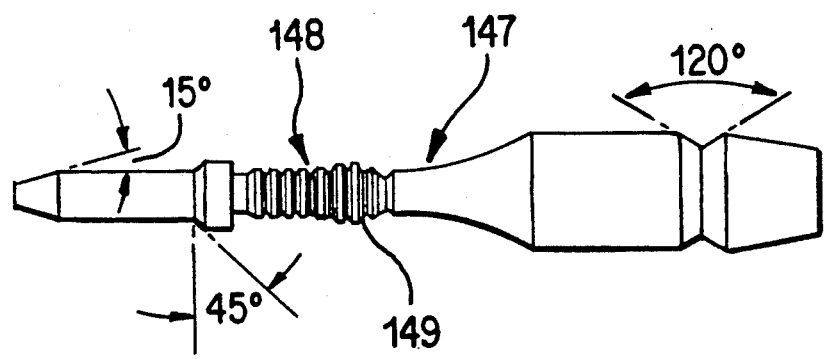
FIG. 29 shows a further special embodiment of a thread formation on the shaft of the pin or bolt.
Figure 30:
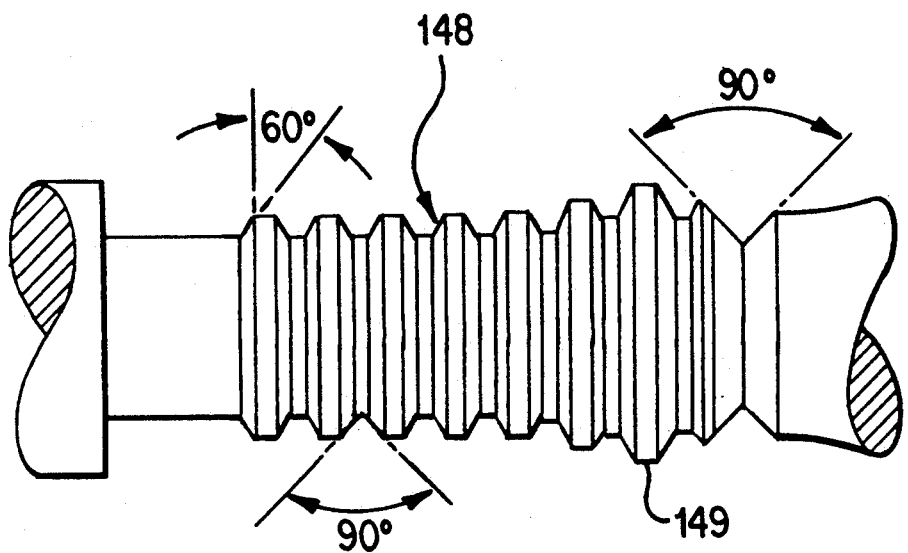
FIG. 30 shows the structure of the thread according to FIG. 29 in detail.

Pin or bolt 147 according to FIG. 29 has a central thread section 148, which is provided with a thread increasing continuously in diameter up to the maximum diameter 149 towards the head of the pin and decreasing from the maximum thread diameter 149 to the original diameter. The structure of the thread is shown in detail in FIG. 30.

FIG. 31 shows an embodiment of this invention for connecting precision elements in the dental field, for example an attachment device. A crown 150 is provided with an attachment element 151, the T-shaped recess 152 of which has a counter element 153 as a connection; the opposite end 154 of the counter element 153 is arranged as a toothing, which is in engagement with a counter toothing 155 as the end of a metal base 156 according to male and female elements. The two toothings 154 and 155 are provided with bond-assisting layers, which undergo a chemical bond with each other in the way explained in connection with the preceeding embodiments. Instead of the shown toothings 154, 155 the counter element can be provided with a ring 157 forming the end of the metal base 156.

What I claim is:

1. A supporting mechanical connecting system for use in the dental and medical fields, comprising:
   a prefabricated connecting element made from a high-strength material, said connecting element coated with a substantially non-metallic, hydrolysis-stable bond-assisting layer; and
   a non-deformable prefabricated receiving element for connecting to an organic or prosthetic portion of a living organism for providing a mechanical connection between said connecting element and the living organism, said receiving element made from a high-strength material, the non-metallic, hydrolysis-stable bond-assisting layer of said connecting element producing a hydrolysis-stable chemical or physical bond with said receiving element.

2. The supporting mechanical connecting system according to claim 1, wherein said connecting element has a cylindrical shaft having a free end, a circular taper extending conically towards said free end, and a circular, in cross section, U-shaped recess extending from the free end inwardly, and wherein this shape is chosen so that a reduction of tension is obtained.

3. The supporting mechanical connecting system according to claim 2, wherein said cylindrical shaft changes into an outwardly extending, in cross section circular, conical shape, which is joined by said circular, conical tapering.

4. The supporting mechanical connecting system according to claim 2, wherein the head portion of said receiving element starting from the cylindrical shaft is provided as a grid, especially made from titanium, the grating constant being approximately 200-300 $\mu$.

5. The supporting mechanical connecting system according to claim 4, wherein titanium plasma, hydroxylapatite, tricalcium phosphate or similar biocompatible material is applied to said system, and the size of the pores is approximately 200-300 $\mu$.

6. The supporting mechanical connecting system according to claim 1, wherein the surface of said connecting element is partially roughened, and whereby the degree of roughening (average value of roughness) is optimized in view of the strength of the material to be anchored.

7. The supporting mechanical connecting system according to claim 1, wherein said connecting element has a cylindrical shaft, a circular taper extending conically towards the free end, and a circular, in cross section, U-shaped recess extending from said free end inwardly, whereby this shape is chosen so that a reduction of the tension is obtained, and wherein said connecting element is roughened at least over part of its surface, and whereby the degree of roughening is optimized in view of the strength of the material to be anchored.

8. The supporting mechanical connecting system according to claim 1, wherein said connecting element is a system of two tubes fitted telescopically one into the other, the tube of larger diameter is provided with a bond-assisting layer on its inner surface, and the tube of smaller diameter is provided with a bond-assisting layer on its outer surface so that both tubes when moved telescopically one into the other undergo a chemical or physical-chemical hydrolysis-stable bond by means of the bond-assisting layers.

9. The supporting mechanical connecting system according to claim 1, wherein said bond-assisting layer is provided with a plastics layer applied onto said bond-assisting layer, which undergoes a chemical bond with said bond-assisting layer and the material of said receiving element.

10. The supporting mechanical connecting system according to claim 1, wherein several bond-assisting layers are applied onto said connecting element, the sequence and composition of the layers being chosen so that they result in an increased retention force and to control a physical parameter of the materials being involved in the bonding.

11. The supporting mechanical connecting system according to claim 10, wherein all of said bond-assisting layers are chosen so that the physical parameters of the materials being involved in the bond, result in an increased retention force.

12. The supporting mechanical connecting system according to claim 10, wherein said bond-assisting layers are formed with different thicknesses at different locations, and the thicknesses of said layers vary from layer to layer in order to be able to control various physical parameters.

13. The supporting mechanical connecting system according to claim 1, wherein said connecting element is a pin, the outer end of said pin is formed as a screw head for receiving a screwing tool having a tool head and a shaft, wherein the tool head or at the shaft is provided with a breaking point at which position the tool head can be separated from the shaft.

14. The supporting mechanical connecting system according to claim 13, wherein said pin is widened at one end, at which place a coating is provided of said bond-assisting layer to form a chemical bond with the receiving element.

15. The supporting mechanical connecting system according to claim 14, wherein said pin is widened to form a punch plate, the base surface of said punch plate is formed as an extending arrow and said surface is coated with said bond-assisting layer.

16. The supporting mechanical connecting system according to claim 13, wherein said pin is provided with a safety ring at the underside of the screw head, said ring is fastened to the screw head and the underside of which is in contact with said receiving element, and wherein said side of said receiving element facing said safety ring is provided with a corresponding safety ring.

17. The supporting mechanical connecting system according to claim 1, wherein said connecting element provided with said bond-assisting layer is used to anchor a tooth structure.

18. The supporting mechanical connecting system according to claim 1, wherein the peripheral surface of said connecting element is provided with a roughness profile, which is optimized in view of its dimensions and strength characteristics of said connecting element.

19. Element according to claim 18, wherein for glass ionomer cements the roughness of the surface of the pin with its maximum value ($R_t$) is between 5,20 and 5,50 $\mu$, with its average value ($R_a$) is between 0.8 and 1,6 $\mu$, and below a quotient from 1:6 until 1:8 of pin to filling material the roughness can be up to 11,0 $\mu R_t$ or 4,0 $\mu R_a$.

20. Element according to claim 18, wherein for plastics components the roughness of the pin surface with its maximum value is between 5,50 and 20 $\mu$ and with its average value between 1,6 and 5,5 $\mu$, and with a quotient below 1:6 until 1:8 of pin to filling material the roughness can be up to 60 $\mu R_t$ or 11,5 $\mu R_a$.

21. Element according to claim 18, wherein for amalgam the roughness of the pin surface with its maximum value is between 30 and 90 $\mu$ and with its average value is between 8 and 16 $\mu$.

22. Device for connecting precision elements in the dental field, f.e. arrangements or telescopic crowns on metal base, by using a connecting element according to claim 1 wherein the portions of the connecting device are formed as male or female elements intermeshing with each other, and are coated with a pourable layer at a predetermined location for being connected to the metal crown or metal base, whereby preferably the coating on the connecting area is made of a hydrolysis-stable bond-assisting layer, f.e. a metal ceramics layer.

23. The supporting mechanical connecting system in accordance with claim 1, wherein said connecting element is provided with a cylindrical shaft having a thread formed on at least a portion of said shaft, and said receiving element is provided with a bore for receiving said shaft.

24. The supporting mechanical connecting system according to claim 23, wherein said cylindrical shaft at its lower end is arranged downwardly and conically widening and subsequent thereto, inwardly and upwardly widening, or alternatively is arranged planar.

25. The supporting mechanical connecting system according to claim 24, wherein the cylindrical shaft at its lower end widens from a diameter $D_1=0,9$ x to a diameter $D_2=1,14$ x over a length $L_1=0,8$ x in a conical manner, subsequent thereto decreases in diameter over a length $L_2=0,15$ x in an angle of about 45°, and widens with an opening angle of about 120° inwardly, whereby x is a length factor.

26. The supporting mechanical connecting system according to claim 23, wherein said thread section extending in the longitudinal axis of the system is provided with a thread diameter increasing in a direction opposite to the screwing direction.

27. The supporting mechanical system in accordance with claim 23, wherein said connecting element is provided with a screw head at its upper end.

28. The supporting mechanical connecting system in accordance with claim 1, wherein portions of said connecting elements are formed as male or female elements intermeshing with each other, and are coated with a pourable layer at a predetermined location, whereby preferably the coating on the connecting area is made of a hydrolysis-stable bond-assisting layer, such as a metal ceramics layer.

* * * * *